US012800561B2

(12) United States Patent
Kubo et al.

(10) Patent No.: US 12,800,561 B2
(45) Date of Patent: Nov. 17, 2026

(54) CONVERSION DEVICE, PREDICTION MODEL PREPARATION DEVICE, CONVERSION INFORMATION PREPARATION METHOD, PREDICTION MODEL PREPARATION METHOD, AND PROGRAM

(71) Applicant: Komi Hakko Corporation, Osaka (JP)

(72) Inventors: Kenji Kubo, Osaka (JP); Sho Sato, Kyoto (JP); Naoto Asai, Minoo (JP)

(73) Assignee: KOMI HAKKO CORPORATION, Osaka (JP)

( * ) Notice: Subject to any disclaimer, the term of this patent is extended or adjusted under 35 U.S.C. 154(b) by 411 days.

(21) Appl. No.: 18/278,685

(22) PCT Filed: Feb. 28, 2022

(86) PCT No.: PCT/JP2022/008416

§ 371 (c)(1),
(2) Date: Aug. 24, 2023

(87) PCT Pub. No.: WO2022/181819

PCT Pub. Date: Sep. 1, 2022

(65) Prior Publication Data

US 2024/0142423 A1 May 2, 2024

(30) Foreign Application Priority Data

Feb. 26, 2021 (JP) ................................ 2021-031067

(51) Int. Cl.
*G01N 33/00* (2006.01)

(52) U.S. Cl.
CPC ..... *G01N 33/0034* (2013.01); *G01N 33/0063* (2013.01); *G01N 33/0068* (2024.05)

(58) Field of Classification Search
None
See application file for complete search history.

(56) References Cited

U.S. PATENT DOCUMENTS

2005/0208673 A1 9/2005 Labreche et al.
2006/0172279 A1 8/2006 Smela et al.
(Continued)

FOREIGN PATENT DOCUMENTS

CN 111344406 A 6/2020
CN 111386280 A 7/2020
(Continued)

OTHER PUBLICATIONS

SIPA 1st Office Action for corresponding CN Application No. 202280017252.8; Issued Aug. 28, 2025.
(Continued)

*Primary Examiner* — Daniel S Larkin
(74) *Attorney, Agent, or Firm* — CANTOR COLBURN LLP

(57) ABSTRACT

A conversion device converts output information, which is output from a device having a predetermined gas detection function with respect to a predetermined odor molecule, into quantified data of an odorant receptor. The conversion device comprises a conversion unit that uses a prediction model, which has been subjected to machine learning using, as explanatory variables, pieces of output information output from a device having a plurality of gas detection functions with respect to a plurality of respective odor molecules and using, as objective variables, pieces of response information indicating a plurality of responses of the odorant receptor with respect to the plurality of respective odor molecules, to convert the acquired output information into response information indicating a response of the odorant receptor.

9 Claims, 9 Drawing Sheets

(56) References Cited

U.S. PATENT DOCUMENTS

| | | | |
|---|---|---|---|
| 2019/0082722 | A1 | 3/2019 | Sakaki |
| 2020/0124577 | A1 | 4/2020 | Kuroki et al. |
| 2020/0240978 | A1 | 7/2020 | Kuroda |
| 2021/0018479 | A1 | 1/2021 | Watanabe et al. |
| 2022/0309397 | A1 | 9/2022 | Yamada et al. |
| 2023/0090065 | A1 | 3/2023 | Tamura et al. |

FOREIGN PATENT DOCUMENTS

| | | | |
|---|---|---|---|
| CN | 112285312 | A | 1/2021 |
| EP | 1566633 | A1 | 8/2005 |
| EP | 2873971 | A1 | 5/2015 |
| JP | 2002524205 | A | 8/2002 |
| JP | 2006507507 | A | 3/2006 |
| JP | 2020073930 | A | 5/2020 |
| TW | 410274 | B | 11/2000 |
| WO | 0015269 | A1 | 3/2000 |
| WO | 200015268 | A1 | 3/2000 |
| WO | 2004048937 | A2 | 6/2004 |
| WO | 2014188419 | A1 | 11/2014 |
| WO | 2017085796 | A1 | 5/2017 |
| WO | 2017159765 | A1 | 9/2017 |
| WO | 2018235148 | A1 | 12/2018 |
| WO | 2019035476 | A1 | 2/2019 |
| WO | 2019036432 | A1 | 2/2019 |
| WO | 2019163966 | A1 | 8/2019 |
| WO | 2020255305 | A1 | 12/2020 |
| WO | 2021192915 | A1 | 9/2021 |

OTHER PUBLICATIONS

Bayburt et al., "Self-Assembly of Discoidal Phospholipid Bilayer Nanoparticles with Membrane Scaffold Proteins", Nano Letters, 2002, vol. 2 (8), pp. 853-856.

Civjan et al., "Direct solubilization of heterologously expressed membrane proteins by incorporation into nanoscale lipid bilayers" Biotechniques, Sep. 2003, 35 (3), pp. 556-560, 562-563.

International Search Report for International Application No. PCT/JP2022/008416; Date of Mailing, May 17, 2022.

Yang et al., "Nanodisc-Based Bioelectronic Nose Using Olfactory Receptor Produced in *Escherichia coli* for the Assessment of the Death-Associated Odor Cadaverine", ACS Nano, Dec. 26, 2017, 11 (12), pp. 11847-11855.

EPO Extended European Search Report for corresponding EP Application No. 22759852.1; Issued Nov. 18, 2024.

International Search Report issued Apr. 11, 2023 in International (PCT) Application No. PCT/JP2023/007331.

TW Office Action for corresponding TW Application No. I848272; Issued Jan. 7, 2023.

EPO The Partial Supplementary European Search Report for corresponding EP Application No. 23760212.3; Issued Jun. 5, 2026.

SIPO Decision of Refusal for corresponding CN Application No. 202280017252.8; Issued Jun. 26, 2026.

CONVERSION DEVICE, PREDICTION MODEL PREPARATION DEVICE, CONVERSION INFORMATION PREPARATION METHOD, PREDICTION MODEL PREPARATION METHOD, AND PROGRAM

CROSS REFERENCE TO RELATED APPLICATIONS

This is the U.S. national stage of application No. PCT/JP2022/008416, filed on Feb. 28, 2022. Priority under 35 U.S.C. § 119 (a) and 35 U.S.C. § 365 (b) is claimed from Japanese Application No. 2021-031067, filed Feb. 26, 2021, the disclosure of which is also incorporated herein by reference.

TECHNICAL FIELD

The present invention relates to a conversion device, a prediction model preparation device, a conversion information preparation method, a prediction model preparation method, and a program.

BACKGROUND ART

A conventionally known device has a gas detection capability for outputting an electrical signal according to the type of gas detected. A gas sensor is a known example of a gas detection-capable device. The gas sensor outputs an electrical signal according to the odor of gas detected. Some systems have been proposed that identify the type of odor using such a gas sensor (see, for example, Patent Document 1 and Patent Document 2).

Patent Document 1: PCT International Publication No. WO2017/085796

Patent Document 2: PCT International Publication No. WO2018/235148

DISCLOSURE OF THE INVENTION

Problems to be Solved by the Invention

Incidentally, there are various analysis methods for gas detection-capable devices. Analysis methods can therefore differ among gas detection-capable devices. In some cases, it is difficult to establish a correlation between output data outputted from gas detection-capable devices that adopt different analysis methods. For example, in a case where mixed odor is analyzed, it can be difficult to establish such a correlation. The value of odor data (electrical signals) obtained through some old-type gas detection-capable devices can therefore diminish with evolution or modification of gas detection-capable devices. In this regard, it is preferable to be able to establish a correlation between different gas detection-capable devices.

The present invention was made in view of the foregoing problems, and an object thereof is to provide a conversion device, a prediction model preparation device, a conversion information preparation method, a prediction model preparation method, and a program that make it possible to establish a correlation between different gas detection-capable devices.

Means for Solving the Problems

The present invention relates to a conversion device for converting output information outputted from a specific gas detection-capable device for a specific odor molecule into response information indicating a response of an olfactory receptor, the conversion device including: an output information acquisition unit configured to acquire output information outputted from a gas detection-capable device for a specific odor molecule; a conversion unit configured to convert the acquired output information into response information based on output signals outputted from a plurality of gas detection-capable devices respectively corresponding to a plurality of odor molecules and response information indicating responses of a plurality of olfactory receptors respectively corresponding to the plurality of odor molecules; and an output unit configured to output the response information obtained through the conversion.

Preferably, the conversion unit converts the acquired output information into response information indicating a response of an olfactory receptor using a prediction model trained through machine learning using output information outputted from the plurality of gas detection-capable devices respectively corresponding to the plurality of odor molecules as an explanatory variable and the response information indicating responses of the olfactory receptors respectively corresponding to the plurality of odor molecules as a target variable.

Preferably, the conversion unit uses a prediction model trained through machine learning using, as an explanatory variable, a numerical value, a function, or a spatial or temporal indicator that is calculated using a mathematical, statistical, or machine learning technique from the output information outputted from each of the gas detection-capable devices, or a variable newly created through feature engineering.

Preferably, the conversion unit uses a prediction model trained through machine learning using, as a target variable, a numerical value, a function, or a spatial or temporal indicator that is calculated using a mathematical, statistical, or machine learning technique from the response information of each of the olfactory receptors, or a variable newly created through feature engineering.

Preferably, the conversion unit converts the acquired output information into response information using a prediction model trained through machine learning using time-series data and the number of feature patterns from the output information outputted from each of the plurality of gas detection-capable devices as an explanatory variable, and time-series data and the number of feature patterns from the response information of the plurality of olfactory receptors as a target variable.

Preferably, the conversion unit uses a prediction model trained through machine learning using, as an explanatory variable, the presence or absence of output information from each of the plurality of gas detection-capable devices.

Preferably, the conversion unit uses a prediction model trained through machine learning using, as a target variable, the presence or absence of a response of each of a plurality of receptors included in the olfactory receptors.

Preferably, the conversion unit uses a prediction model trained through machine learning using, as an explanatory variable, mass-to-charge ratio and intensity based on the output information outputted from each of the gas detection-capable devices.

Preferably, the conversion device further includes an estimation unit configured to estimate a descriptor representing a characteristic of the specific odor from the response information obtained through the conversion, and the output unit outputs the thus estimated descriptor.

The present invention also relates to a conversion device for converting response information indicating a response of an olfactory receptor to a specific odor molecule into output information to be outputted from a gas detection-capable device, the conversion device including: a response information acquisition unit configured to acquire response information indicating a response of an olfactory receptor to a specific odor molecule; a conversion unit configured to convert the acquired response information into output information to be outputted from a gas detection-capable device using a prediction model trained through machine learning using response information indicating responses of a plurality of olfactory receptors respectively corresponding to a plurality of odor molecules as an explanatory variable and output information outputted from a plurality of gas detection-capable devices respectively corresponding to the plurality of odor molecules as a target variable; and an output unit configured to output the output information obtained through the conversion.

The present invention also relates to a prediction model preparation device for preparing a prediction model for converting output information outputted from a gas detection-capable device for a specific odor molecule into response information indicating a response of an olfactory receptor, the prediction model preparation device including: an explanatory variable acquisition unit configured to acquire, as an explanatory variable, output information outputted from a plurality of gas detection-capable devices respectively corresponding to a plurality of odor molecules; a target variable acquisition unit configured to acquire, as a target variable, response information indicating responses of a plurality of olfactory receptors respectively corresponding to the plurality of odor molecules; and a prediction model preparation unit configured to prepare a prediction model by applying the acquired explanatory variable and the acquired target variable to machine learning.

The present invention also relates to a prediction model preparation device for preparing a prediction model for converting response information indicating a response of an olfactory receptor to a specific odor molecule into output information to be outputted from a gas detection-capable device, the prediction model preparation device including: an explanatory variable acquisition unit configured to acquire, as an explanatory variable, response information indicating responses of a plurality of olfactory receptors respectively corresponding to a plurality of odor molecules; a target variable acquisition unit configured to acquire, as a target variable, output information outputted from a plurality of gas detection-capable devices respectively corresponding to the plurality of odor molecules; and a prediction model preparation unit configured to prepare a prediction model by applying the acquired explanatory variable and the acquired target variable to machine learning.

The present invention also relates to a conversion information preparation method for preparing conversion information by converting output information outputted from a specific gas detection-capable device for a specific odor molecule into response information indicating a response of an olfactory receptor, the conversion information preparation method including: an output information acquisition step for acquiring output information outputted from a gas detection-capable device for a specific odor molecule; a conversion step for converting the acquired output information into response information indicating a response of an olfactory receptor using a prediction model trained through machine learning using output information outputted from a plurality of gas detection-capable devices respectively corresponding to a plurality of odor molecules as an explanatory variable and response information indicating responses of a plurality of olfactory receptors respectively corresponding to the plurality of odor molecules as a target variable; and an output step for outputting, as conversion information, the response information obtained through the conversion.

The present invention also relates to a conversion information preparation method for preparing conversion information by converting response information indicating a response of an olfactory receptor to a specific odor molecule into output information to be outputted from a gas detection-capable device, the conversion information preparation method including: a response information acquisition step for acquiring response information indicating a response of an olfactory receptor to a specific odor molecule; a conversion step for converting the acquired response information into output information to be outputted from a gas detection-capable device using a prediction model trained through machine learning using response information indicating responses of a plurality of olfactory receptors respectively corresponding to a plurality of odor molecules as an explanatory variable and output information outputted from a plurality of gas detection-capable devices respectively corresponding to the plurality of odor molecules as a target variable; and an output step for outputting the converted response information as conversion information.

The present invention also relates to a prediction model preparation method for preparing a prediction model for converting output information outputted from a gas detection-capable device for a specific odor molecule into response information indicating a response of an olfactory receptor, the prediction model preparation method including: an explanatory variable acquisition step for acquiring, as an explanatory variable, output information outputted from a plurality of gas detection-capable devices respectively corresponding to a plurality of odor molecules; a target variable acquisition step for acquiring, as a target variable, response information indicating responses of a plurality of olfactory receptors respectively corresponding to the plurality of odor molecules; and a prediction model preparation step for preparing a prediction model by applying the acquired explanatory variable and the acquired target variable to machine learning.

The present invention also relates to a prediction model preparation method for preparing a prediction model for converting response information indicating a response of an olfactory receptor to a specific odor molecule into output information to be outputted from a gas detection-capable device, the prediction model preparation method including: an explanatory variable acquisition step for acquiring, as an explanatory variable, response information indicating responses of a plurality of olfactory receptors respectively corresponding to a plurality of odor molecules; a target variable acquisition step for acquiring, as a target variable, output information outputted from a plurality of gas detection-capable devices respectively corresponding to the plurality of odor molecules; and a prediction model preparation step for preparing a prediction model by applying the acquired explanatory variable and the acquired target variable to machine learning.

The present invention also relates to a program for causing a computer to operate as a conversion device for converting output information outputted from a specific gas detection-capable device for a specific odor molecule into response information indicating a response of an olfactory receptor, the program being configured to cause the computer to function as: an output information acquisition unit configured to acquire output information outputted from a gas detection-capable device for a specific odor molecule; a conversion unit configured to convert the acquired output information into response information indicating a response of an olfactory receptor using a prediction model trained through machine learning using output information outputted from a plurality of gas detection-capable devices respectively corresponding to a plurality of odor molecules as an explanatory variable and response information indicating responses of a plurality of olfactory receptors respectively corresponding to the plurality of odor molecules as a target variable; and an output unit configured to output the response information obtained through the conversion.

The present invention also relates to a program for causing a computer to function as a conversion device for converting response information indicating a response of an olfactory receptor to a specific odor molecule into output information to be outputted from a gas detection-capable device, the program being configured to cause the computer to function as: an output information acquisition unit configured to acquire response information indicating a response of an olfactory receptor to a specific odor molecule; a conversion unit configured to convert the acquired response information into output information to be outputted from a gas detection-capable device using a prediction model trained through machine learning using response information indicating responses of a plurality of olfactory receptors respectively corresponding to a plurality of odor molecules as an explanatory variable and output information outputted from a plurality of gas detection-capable devices respectively corresponding to the plurality of odor molecules as a target variable; and an output unit configured to output the response information obtained through the conversion.

The present invention also relates to a program for causing a computer to function as a prediction model preparation device for preparing a prediction model for converting output information outputted from a gas detection-capable device for a specific odor molecule into response information indicating a response of an olfactory receptor, the program being configured to cause the computer to function as: an explanatory variable acquisition unit configured to acquire, as an explanatory variable, output information outputted from a plurality of gas detection-capable devices respectively corresponding to a plurality of odor molecules; a target variable acquisition unit configured to acquire, as a target variable, response information indicating responses of a plurality of olfactory receptors respectively corresponding to the plurality of odor molecules; and a prediction model preparation unit configured to prepare a prediction model by applying the acquired explanatory variable and the acquired target variable to machine learning.

A program for causing a computer to function as a prediction model preparation device for preparing a prediction model for converting response information indicating a response of an olfactory receptor to a specific odor molecule into output information to be outputted from a gas detection-capable device, the program being configured to cause the computer to function as:

an explanatory variable acquisition unit configured to acquire, as an explanatory variable, response information indicating responses of a plurality of olfactory receptors respectively corresponding to a plurality of odor molecules;

a target variable acquisition unit configured to acquire, as a target variable, output information outputted from a plurality of gas detection-capable devices respectively corresponding to the plurality of odor molecules; and a prediction model preparation unit configured to prepare a prediction model by applying the acquired explanatory variable and the acquired target variable to machine learning.

Effects of the Invention

According to the present invention, it is possible to provide a conversion device, a prediction model preparation device, a conversion information preparation method, a prediction model preparation method, and a program that make it possible to establish a correlation between different gas detection-capable devices.

EXPLANATION OF REFERENCE NUMERALS

Figure 1:
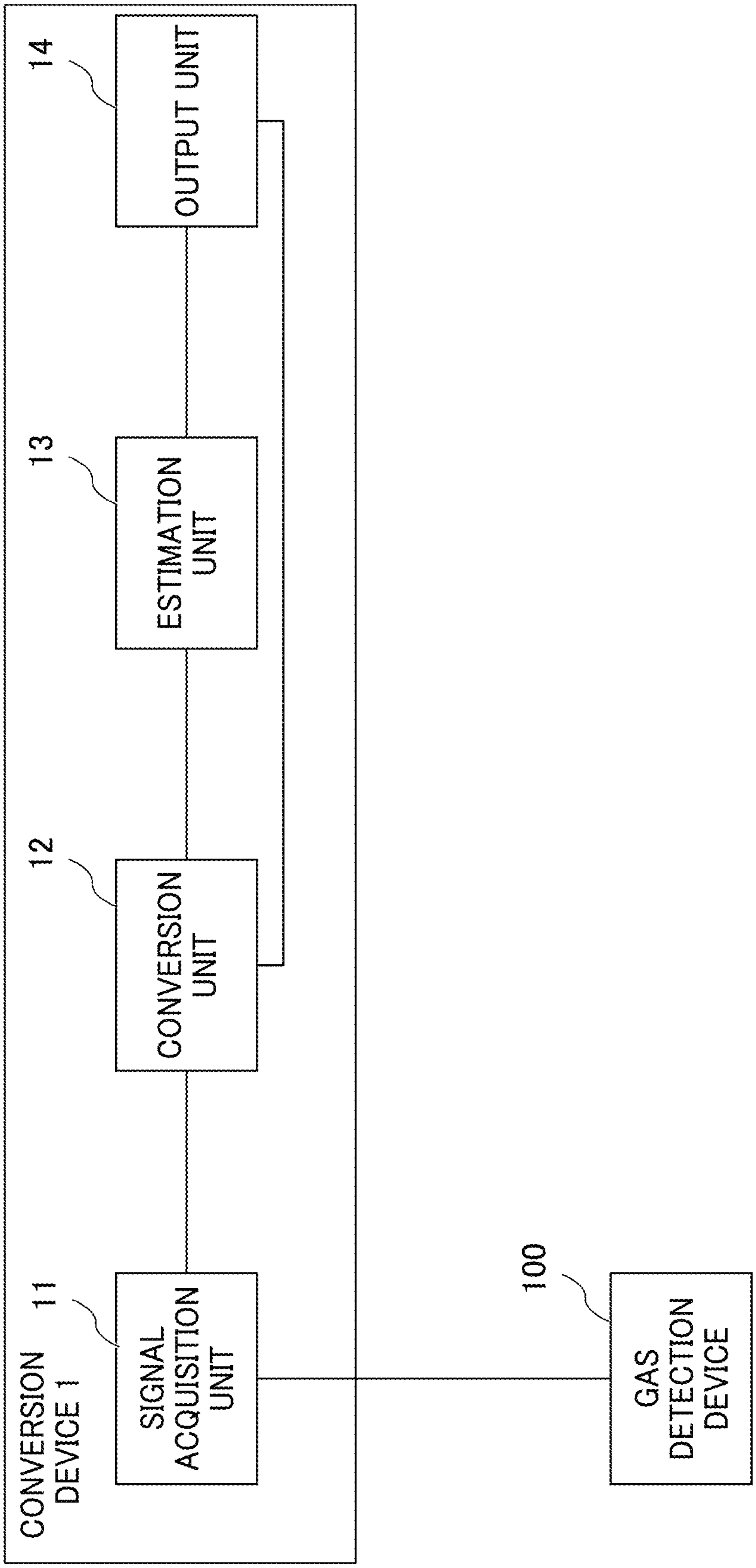
FIG. 1 is a block diagram illustrating a configuration of a conversion device according to a first embodiment of the present invention.

1: Conversion device
2: Prediction model preparation device
11: Output information acquisition unit
12: Conversion unit
13: Estimation unit
14: Output unit
21: Explanatory variable acquisition unit
22: Target variable acquisition unit
23: Prediction model preparation unit

100: Gas detection device
200: Olfactory receptor

PREFERRED MODE FOR CARRYING OUT THE INVENTION

The following describes a conversion device 1, a prediction model preparation device, a conversion information preparation method, a prediction model preparation method, and a program according to some embodiments of the present invention with reference to FIGS. 1 to 9. First, an overview of the conversion device 1 is described prior to describing the conversion device 1, the prediction model preparation device 2, the conversion information preparation method, the prediction model preparation method, and the program according to each embodiment.

First, the purpose of using the conversion device 1 is described. The use of a gas sensor has been proposed as a system for identifying types of odor. However, it is difficult to accurately differentiate and identify types of odor perceived by humans by relying solely on a gas sensor. This is because a detection element of the gas sensor is composed of a substance that is not in line with the human sense (olfaction). It is therefore difficult to identify and differentiate types of odor, even if various detection elements and analysis methods are proposed.

Although there is an approach of somehow linking information from outputs of a gas sensor and information from human sensory testing through machine learning, for example, highly accurate determination based on such an approach has not yet been achieved because sensory testing data exhibits variations in evaluations among human individuals. There is also an approach of adopting a representation method that converts chemical structures of molecules into alphanumeric strings, such as SMILES notation, to enhance the correlation between outputs of a gas sensor and results of sensory testing. These approaches have led to an improvement in prediction accuracy but are not enough to accurately determine, differentiate, and predict types of odor due to the fact that information from odorless molecules is also included. However, expressing outputs of a gas sensor as quantitative values that reflect human olfaction, if possible, makes it feasible to accurately determine odor based on human olfaction.

The conversion device 1 converts, for example, output information outputted from a specific gas detection-capable device (also referred to below as a gas detection device 100) for a specific odor molecule into response information indicating a response of an olfactory receptor. Thus, the conversion device 1 converts output information having different values outputted from different gas detection devices 100 that adopt different analysis methods for the same odor molecule into a single type of response information that indicates responses of olfactory receptors 200, providing consistent results. This configuration allows the conversion device 1 to associate output information from the gas detection devices 100 with a single type of response information, regardless of the difference in analysis methods between the gas detection devices 100. For example, the conversion device 1 achieves the association of output information that varies in values and units for the same odor molecule among a plurality of gas detection devices 100 using a single type of response information as what may be referred to as an "odor measurement reference". In the following embodiment, the conversion device 1 converts output information into response information using a learning model trained through machine learning.

The following describes the gas detection devices 100. Each gas detection device 100 is, for example, a gas sensor or a mass spectrometer (gas chromatograph-mass spectrometer). Depending on the type and concentration of a specific odor molecule, the gas sensor outputs, as output information, a specific electrical signal (for example, a voltage value, a resistance value, or a current value), a frequency change, a light wavelength change, or an activation level resulting from exposure of the odor molecule to an olfactory receptor. The gas detection device 100 outputs, for example, an electrical signal having a higher voltage value when detecting a higher concentration of the odor molecule in its vicinity. The mass spectrometer outputs, for example, graph data in the form of a plot indicating mass-to-charge ratio and intensity with respect to the type and concentration of the odor molecule.

The following describes the olfactory receptors 200. The olfactory receptors 200 can be implemented by using, for example, known olfactory receptors disclosed in Japanese Unexamined Patent Application, Publication No. 2011-011869, or the like. The olfactory receptors 200 are, for example, nucleic acids that are mounted on a substrate (not shown). The nucleic acids include those containing genes that code for specific receptors. Multiple types of nucleic acids are present on the substrate, and these different types of nucleic acids are arranged on the substrate with space from each other. By bringing cells into contact with the nucleic acids on the substrate, cells that transiently express olfactory receptors corresponding to the different types of nucleic acids are generated on the spot.

The receptors in this form can undergo changes in cellular states when a test substance is brought into contact with the cells. Specifically, changes in intracellular calcium concentration or intracellular cAMP concentration can occur. These changes can be measured using a cAMP-sensitive dye, a cAMP-sensitive fluorescent protein, a calcium-sensitive dye, or a calcium-sensitive fluorescent protein. For example, activation levels of the receptors can be quantitatively determined by measuring brightness changes using a cAMP-sensitive dye or a cAMP-sensitive fluorescent protein. The activation levels are used as response information indicating responses of the olfactory receptors 200, or response information.

Olfactory receptors may be those from a human, a mammal, an insect, or a nematode. Furthermore, the olfactory receptors are not limited to a form for responding to a liquid test substance and may take a form for responding to a gaseous test substance (test substance in the form of gas) upon contact. The olfactory receptors in the latter form can be used for either the gas detection devices 100 or the olfactory receptors 200. That is, the conversion device 1 can perform conversion between response information indicating a response of an olfactory receptor to a gaseous test substance and response information indicating a response of an olfactory receptor to a liquid test substance.

The olfactory receptors are not limited to the form that is expressed in the cells and may alternatively take a non-cellular form. For example, liposomes that are formed by lipid bilayers such as cell membranes and that have various olfactory receptors present within the membranes may be arranged on the substrate with space from each other. The size of the liposomes is not particularly limited and may typically be approximately 100 nm in diameter. The production method for the liposomes is not particularly limited and may involve dividing olfactory receptor-expressing cells into a cell membrane fraction (which may contain intracellular signaling proteins such as G proteins, adenylate cyclase, cyclic nucleotide-gated channels) and a cytoplasmic fraction (which may contain intracellular signaling molecules such as GDP, GTP, ATP, and cAMP), and then mixing and stirring the fractions to induce fusion. Alternatively, olfactory receptor proteins may be used as probes on the substrate. In this case, it is preferable to employ nanodiscs that maintain a three-dimensional structure in which the olfactory receptors penetrate the cell membranes. Nanodiscs are, for example, membrane scaffold proteins (MSP) composed of variants of apolipoprotein A1 (APOA1) and allow for assembly of lipid bilayers into disc-shaped structures (Timothy H. Bayburt, Yelena V. Grinkova, and Stephen G. Sligar Nano Letters 2002 2 (8), 853-856). Nanodiscs can therefore retain membrane proteins in a state of penetrating through the lipid membranes even in an extracellular environment (Civjan N R, Bayburt T H, Schuler M A, Sligar S G. Direct solubilization of heterologously expressed membrane proteins by incorporation into nanoscale lipid bilayers. Biotechniques. 2003 September; 35(3):556-60, 562-3). The substrate on which the nanodiscs are arranged is not particularly limited, and may be, for example, a carbon nanotube FET (Yang H, Kim D, Kim J, Moon D, Song H S, Lee M, Hong S, Park T H. Nanodisc-Based Bioelectronic Nose Using Olfactory Receptor Produced in *Escherichia coli* for the Assessment of the Death-Associated Odor Cadaverine. ACS Nano. 2017 Dec. 26; 11(12):11847-11855. doi: 10.1021/acsnano). The production method for the nanodiscs is not particularly limited and may involve expressing and recovering MSP using an organism such as *Escherichia coli*, mixing the MSP with solubilized membrane proteins and phospholipids dissolved in water using a surfactant, removing the surfactant through dialysis or the like, and forming nanodiscs through self-assembly. The activation levels of the receptors can be quantitatively evaluated also by measuring changes in current, voltage, impedance, or other parameters caused by the test substance using these olfactory receptors in the non-cellular form.

First Embodiment

The following describes a conversion device 1, a conversion information preparation method, and a program according to a first embodiment of the present invention with reference to FIGS. 1 to 6. It should be noted that gas sensors are described as an example of gas detection devices 100 in the present embodiment.

The conversion device 1 converts output information outputted from a specific gas detection device 100 for a specific odor molecule into response information indicating a response of an olfactory receptor 200. The conversion device 1 according to the present embodiment outputs the response information obtained through the conversion and outputs a word (descriptor) representing a characteristic of the specific odor based on the response information obtained through the conversion. As illustrated in FIG. 1, the conversion device 1 includes an output information acquisition unit 11, a conversion unit 12, an estimation unit 13, and an output unit 14.

The output information acquisition unit 11 is, for example, implemented through operation of a CPU. The output information acquisition unit 11 acquires output information outputted from a gas detection device 100 for a specific odor molecule. For example, the output information acquisition unit 11 acquires, as output information, a voltage value outputted from the gas detection device 100 that has sensed the specific odor (odor molecule). The output information acquisition unit 11 may acquire, for example, output information measured by a gas detection device 100 at a distant location.

The conversion unit 12 is, for example, implemented through operation of the CPU. The conversion unit 12 converts the acquired output information into response information based on output signals outputted from a plurality of gas detection devices 100 respectively corresponding to a plurality of odor molecules and response information indicating responses of a plurality of olfactory receptors 200 respectively corresponding to the plurality of odor molecules. In the present embodiment, the conversion unit 12 converts the acquired output information into response information indicating a response of an olfactory receptor 200 using a prediction model trained through machine learning using the output information outputted from the plurality of gas detection devices 100 respectively corresponding to the plurality of odor molecules as an explanatory variable and the response information indicating responses of the olfactory receptors 200 respectively corresponding to the plurality of odor molecules as a target variable.

The conversion unit 12 uses, for example, a prediction model trained through machine learning using, as an explanatory variable, a numerical value, a function, or a spatial or temporal indicator that is calculated using a mathematical, statistical, or machine learning technique from the output information outputted from each of the gas detection devices 100, or a variable newly created through feature engineering. Furthermore, the conversion unit 12 uses a prediction model trained through machine learning using, as a target variable, a numerical value, a function, or a spatial or temporal indicator that is calculated using a mathematical, statistical, or machine learning technique from the response information of each of the olfactory receptors 200, or a variable newly created through feature engineering.

For example, the conversion unit 12 converts the acquired output information into response information using a prediction model trained through machine learning using time-series data and the number of feature patterns from the output information outputted from each of the plurality of gas detection devices 100 as an explanatory variable, and time-series data and the number of feature patterns from the response information of each of the plurality of olfactory receptors 200 as a target variable.

The conversion unit 12 in the present embodiment uses a prediction model trained through machine learning using, as an explanatory variable, the presence or absence of output information from each of the plurality of gas detection devices 100. Furthermore, the conversion unit 12 in the present embodiment uses a prediction model trained through machine learning using, as a target variable, the presence or absence of a response of each of a plurality of receptors included in the olfactory receptors 200. Furthermore, the conversion unit 12 in the present embodiment uses a prediction model trained through machine learning using, as an explanatory variable, mass-to-charge ratio and intensity based on the output information outputted from each of the gas detection devices 100. Thus, the conversion unit 12 converts a conversion voltage value indicated by a voltage value, a resistance value, a current value, a frequency change, or a light wavelength change into response information indicating the activation level of an olfactory receptor 200.

The estimation unit 13 is, for example, implemented through operation of the CPU. The estimation unit 13 estimates a descriptor representing a characteristic of the specific odor from the quantified data indicated by the response information obtained through the conversion. For example, the estimation unit 13 estimates, with respect to the response information obtained through the conversion, a descriptor using descriptors associated with different activation levels of the olfactory receptors 200. The estimation unit 13 estimates, for example, a descriptor indicating a characteristic (sensory characteristic) of the specific odor according to an activation level similar to that in the response information. For example, the estimation unit 13 estimates not only the descriptor "sour" but also the descriptor "refreshing" indicating a citrus odor or the descriptor "pungent" indicating an acetic acid-like odor with respect to the response information. The estimation unit 13 estimates, for example, a plurality of descriptors to indicate characteristics of the odor according to an activation level similar to that in the response information.

Note here that, in regard to the estimation unit 13, it is known to identify a substance that contributes to odor components from a signal of a gas detection device 100. However, even the same substances can be different in odor. Taking the odor of oranges for example, each individual orange can have a different odor. That is, for each odor, it is preferable for the device to be capable of outputting words describing the odor, such as those a human being would use to describe the odor. For example, odors of oranges can be "sour", "sweet", "refreshing", "bitter", or "citrusy", and it is preferable for the device to be capable of evaluating the characteristics of the odor of an orange by using descriptors such as strong in sweetness and mild in acidity.

The estimation unit 13 can estimate characteristics indicating sensory characteristics of the odor from the response information indicating a response of an olfactory receptor 200, allowing for a multifaceted representation of the characteristics of the odor. Thus, it is possible to express the characteristics of the odor in a more recognizable manner.

The output unit 14 is, for example, implemented through operation of the CPU. The output unit 14 outputs the response information obtained through the conversion. The output unit 14 also outputs the estimated descriptors. For example, the output unit 14 displays and thus outputs the response information or the estimated descriptors. The output unit 14 outputs, for example, the activation level in the form of a numerical value as response information.

Figure 2:
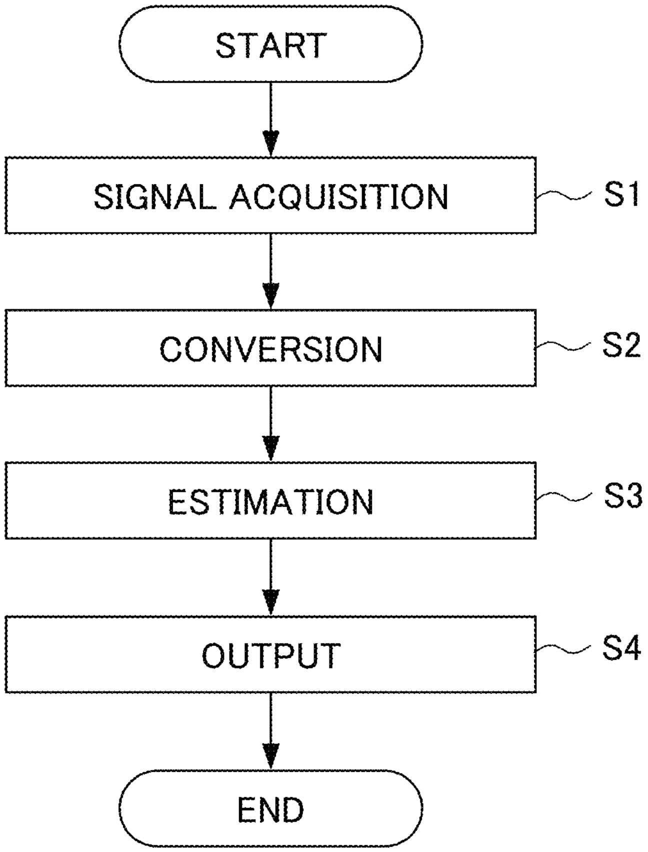
FIG. 2 is a flowchart showing operation of the conversion device according to the first embodiment.

The following describes the flow of operation of the conversion device 1 (conversion information preparation method) with reference to a flowchart shown in FIG. 2. First, the output information acquisition unit 11 acquires a signal for conversion from a gas detection device 100 (Step S1). Next, the conversion unit 12 converts the signal for conversion into response information (Step S2). Next, the estimation unit 13 estimates a descriptor(s) from the response information (Step S3). Next, the output unit 14 outputs the response information and the descriptor (Step S4).

The following describes the program according to the present embodiment. Each of the components included in the conversion device 1 can be implemented by hardware, software, or a combination thereof. Being implemented by software herein means being implemented through a computer reading and executing a program.

The program can be supplied to the computer by being stored on any of various types of non-transitory computer readable media. The non-transitory computer readable media include various types of tangible storage media. Examples of non-transitory computer readable media include magnetic storage media (such as flexible disks, magnetic tape, and hard disk drives), magneto-optical storage media (such as magneto-optical disks), compact disc read only memory (CD-ROM), compact disc recordable (CD-R), compact disc rewritable (CD-R/W), and semiconductor memory (such as mask ROM, programmable ROM (PROM), erasable PROM (EPROM), flash ROM, and random access memory (RAM)). Alternatively, a display program may be supplied to the computer using any of various types of transitory computer readable media. Examples of transitory computer readable media include electrical signals, optical signals, and electromagnetic waves. Such transitory computer readable media are able to supply the program to the computer through a wireless communication channel or a wired communication channel such as electrical wires or optical fibers.

The following describes Examples of the present embodiment.

Example 1

An array sensor including 400 olfactory receptors was used as the olfactory receptors 200. Specific odors were then exposed to olfactory receptor-expressing cells for a predetermined period of time. The concentration of the odors used ranged from 500 μM to 10 μM. The specific odors were also exposed to 12 different gas detection devices 100 (gas sensors) for a predetermined period of time to acquire output information. The output information was then converted into response information using the conversion device 1. The activation levels resulting from the exposure to the olfactory receptor 200-expressing cells were also measured. In Example 1, the following odor molecules were used for the measurement: hexyl acetate, hexyl butyrate, butyl butyrate, 2,7-octadienol, cis-2-penten-1-ol, toluene, beta-ionone, benzothiazole, cyclotene, acetic acid, coumarin, 1,2,4-trimethyl benzene, 2-ethylhexanol, propionaldehyde, 4-Isopropylphenol, Bis (methylthio)methane, 1,2,4,5-tetramethyl benzene, 3-methyl-1-butanol, E-2-nonenal, and m-cresol.

Data processing was performed using Python as a language for a prediction model. The prediction model was evaluated using Random Forest, Support Vector Machine, and Gradient Boosting Decision Tree as algorithms. The prediction model was prepared through regression. Supervised learning was used as a learning method. The coefficient of determination was mainly used for the model evaluation method.

Figure 3:
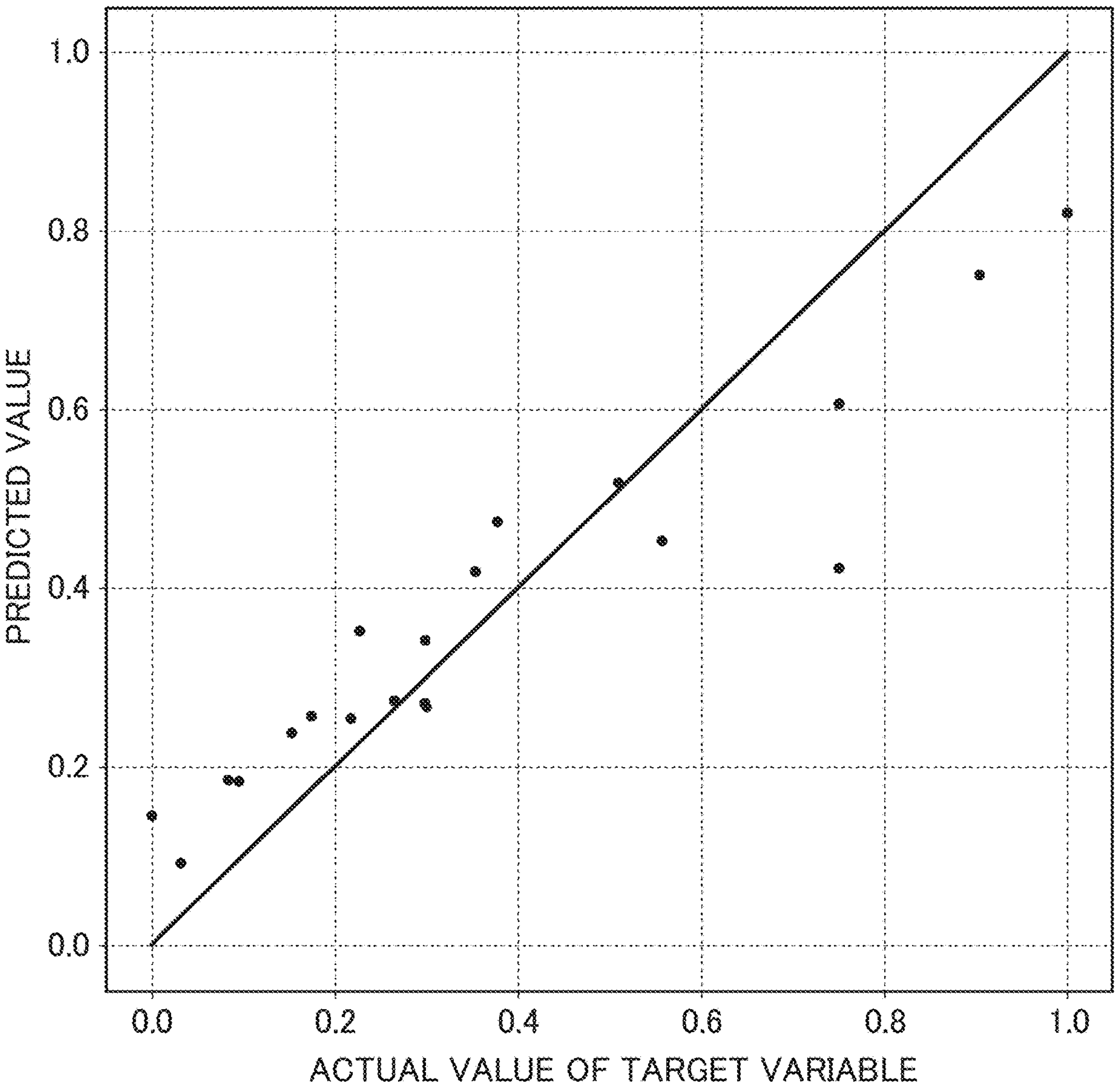
FIG. 3 is an example of a graph showing correlation between values of a target variable predicted through conversion performed using the conversion device according to the first embodiment and values obtained after conversion.

Regression analysis was performed by a Random Forest method, successfully obtaining an R-squared value of 0.834 (with a maximum of 1.0), as shown in FIG. 3 where the vertical axis represents predicted values (response information) outputted from the prediction model and the vertical axis represents actual values of the target variable (activation levels of the olfactory receptor 200-expressing cells).

Figure 4:
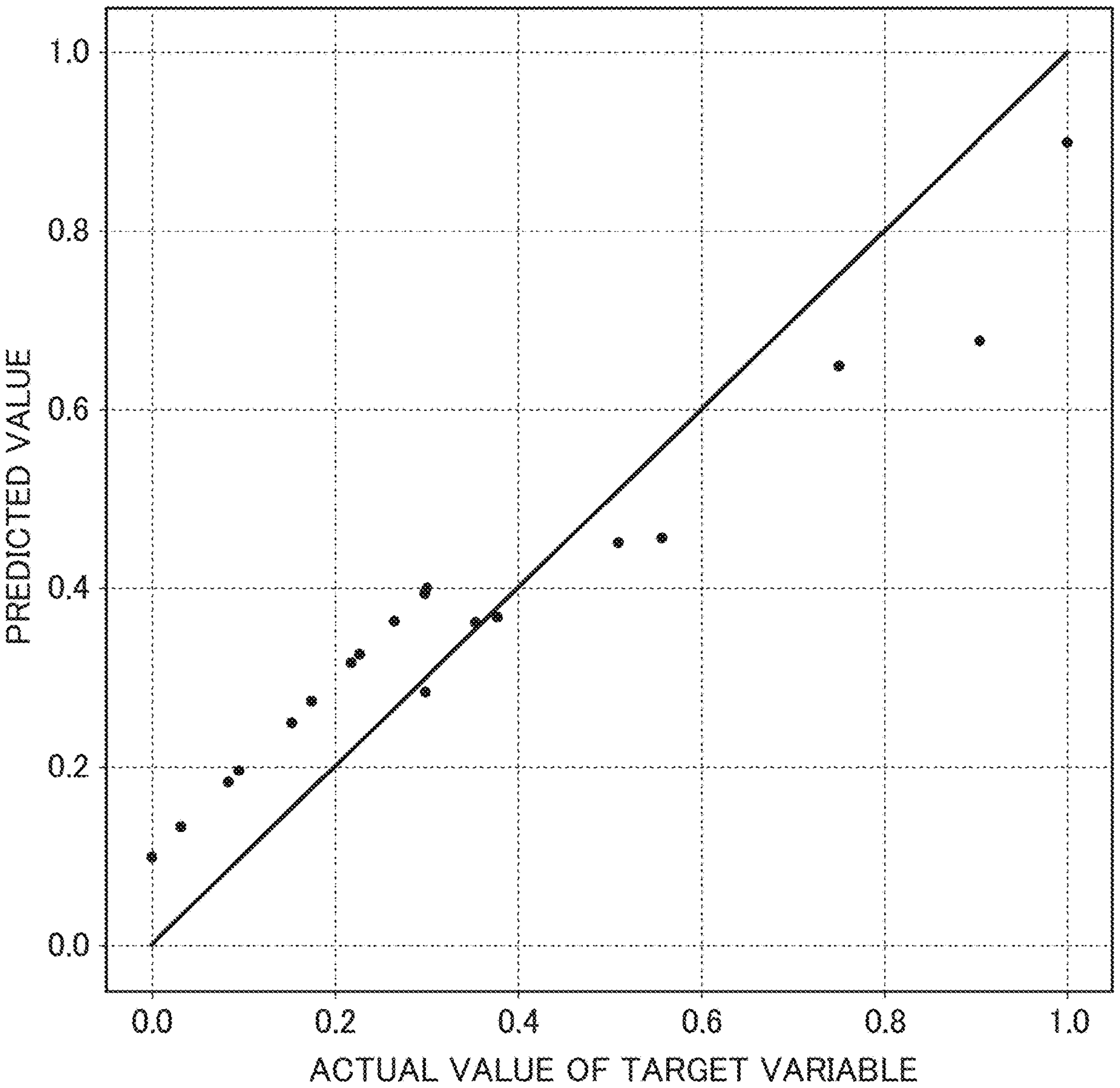
FIG. 4 is another example of a graph showing correlation between values of the target variable predicted through conversion performed using the conversion device according to the first embodiment and values obtained after conversion.
Figure 5:
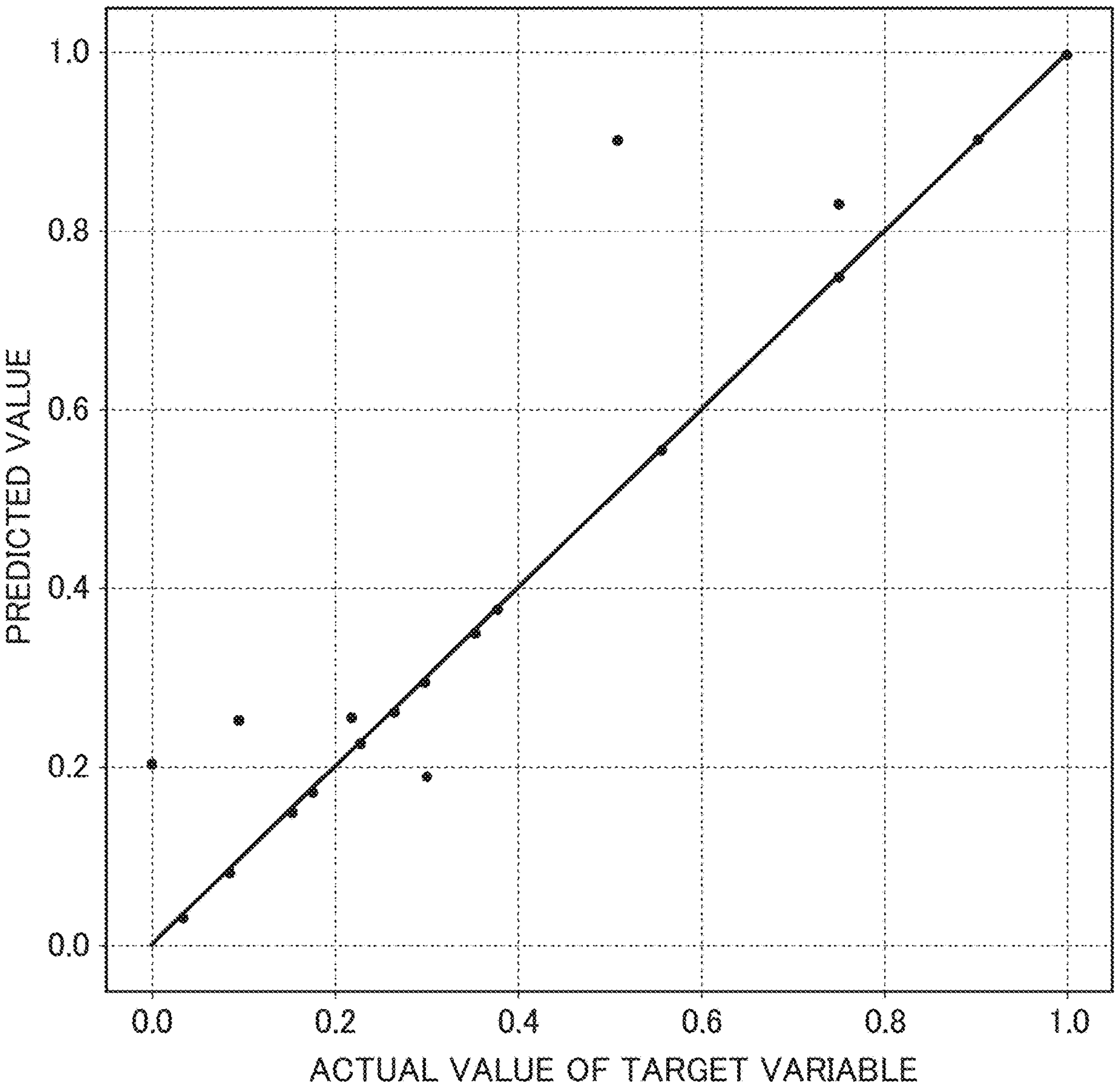
FIG. 5 is a still another example of a graph showing correlation between values of the target variable predicted through conversion performed using the conversion device according to the first embodiment and values obtained after conversion.

Regression analysis was performed using Support Vector Machine, successfully obtaining an R-squared value of 0.871, as shown in FIG. 4. Regression analysis was performed using Gradient Boosting Decision Tree, successfully obtaining an R-squared value of 0.847, as shown in FIG. 5. The analysis results demonstrated that the predicted values were significantly correlated with the actual values of the target variable. That is, the analysis results demonstrated the capability of quantifying the output information.

Example 2

A model was created that is trained using sensor data with respect to specific odor molecules, and that predicts a responsive olfactory receptor 200 and the activation level thereof. The same experimental conditions and procedures as in Example 1 were used for the gas detection devices 100 and the array sensor including the olfactory receptor 200-expressing cells. Data processing was performed through multiclass classification. Python was used as the language. A neural network was used as the algorithm. A multiclass classification model was created in order to establish the relationship between the output information from the gas detection devices 100 and the response information from the olfactory receptors 200. A supervised learning method was employed. The number of hidden layers is not particularly limited and was set to two in the present example. The model was evaluated using overall accuracy (accuracy) and loss function (loss). The output information from the gas detection devices 100 was used as an explanatory variable, and the response information indicating responses of the olfactory receptors 200 was used as a target variable.

Figure 6:
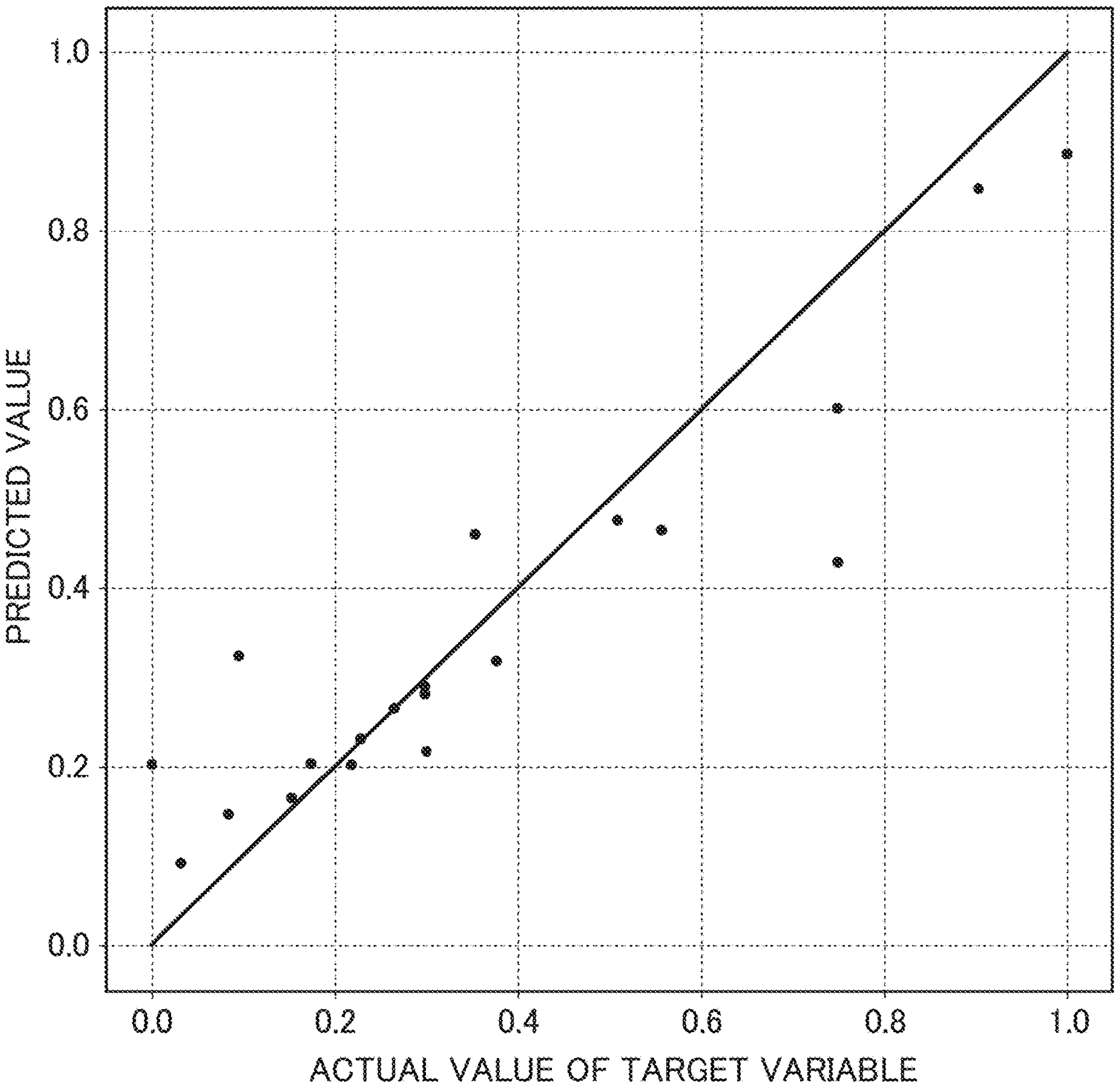
FIG. 6 is a yet another example of a graph showing correlation between values of the target variable predicted through conversion performed using the conversion device according to the first embodiment and values obtained after conversion.

As shown in FIG. 6, at around 500 training iterations, the model achieved and maintained a prediction accuracy of as high as approximately 0.9, and a loss of as low as approximately 0.3 was maintained. The evaluation results demonstrated that the aforementioned prediction model was successfully created.

As described above, the conversion device 1, the conversion information preparation method, and the program according to the first embodiment produce the following effects.

(1) A conversion device 1 for converting output information outputted from a specific gas detection device 100 for a specific odor molecule into response information indicating a response of an olfactory receptor 200, the conversion device including: an output information acquisition unit 11 configured to acquire output information outputted from a gas detection device 100 for a specific odor molecule; a conversion unit 12 configured to convert the acquired output information into response information based on output signals outputted from a plurality of gas detection devices 100 respectively corresponding to a plurality of odor molecules and response information indicating responses of a plurality of olfactory receptors 200 respectively corresponding to the plurality of odor molecules; and an output unit 14 configured to output the response information obtained through the conversion. This configuration makes it possible to convert output information obtained from various gas detection devices 100 into a single type of response information and output the thus obtained response information. This configuration therefore makes it possible to establish a correlation between the gas detection devices 100.

(2) The conversion unit 12 converts the acquired output information into response information indicating a response of an olfactory receptor 200 using a prediction model trained through machine learning using output information outputted from a plurality of gas detection devices 100 respectively corresponding to a plurality of odor molecules as an explanatory variable and response information indicating responses of a plurality of olfactory receptors 200 respectively corresponding to the plurality of odor molecules as a target variable. The use of machine learning allows for a further improvement in the accuracy of the conversion.

(3) The conversion unit 12 uses a prediction model trained through machine learning using, as an explanatory variable, a numerical value, a function, or a spatial or temporal indicator that is calculated using a mathematical, statistical, or machine learning technique from the output information outputted from each of the gas detection devices 100, or a variable newly created through feature engineering. This configuration allows for an improvement in the accuracy of the conversion.

(4) The conversion unit 12 uses a prediction model trained through machine learning using, as a target variable, a numerical value, a function, or a spatial or temporal indicator that is calculated using a mathematical, statistical, or machine learning technique from the response information of each of the olfactory receptors 200, or a variable newly created through feature engineering.

This configuration allows for an improvement in the accuracy of the conversion.

(5) The conversion unit 12 converts the acquired output information into response information using a prediction model trained through machine learning using time-series data and the number of feature patterns from the output information outputted from each of the plurality of gas detection devices 100 as an explanatory variable, and time-series data and the number of feature patterns from the response information of the plurality of olfactory receptors 200 as a target variable. This configuration allows for an improvement in the accuracy of the conversion.

(6) The conversion unit 12 uses a prediction model trained through machine learning using, as an explanatory variable, the presence or absence of output information from each of the plurality of gas detection devices 100. This configuration allows for an improvement in the accuracy of the conversion.

(7) The conversion unit 12 uses a prediction model trained through machine learning using, as a target variable, the presence or absence of a response of each of a plurality of receptors included in the olfactory receptors 200. This configuration allows for an improvement in the accuracy of the conversion.

(8) The conversion device 1 further includes an estimation unit 13 configured to estimate a descriptor representing a characteristic of the specific odor from quantified data indicated by the response information obtained through the conversion, and the output unit 14 outputs the thus estimated descriptor. This configuration makes it possible to provide a descriptor(s) closely representing a characteristic(s) of the odor indicated by the response information. This configuration therefore makes it possible to obtain the response information as sensory information about the odor.

Second Embodiment

Figure 7:
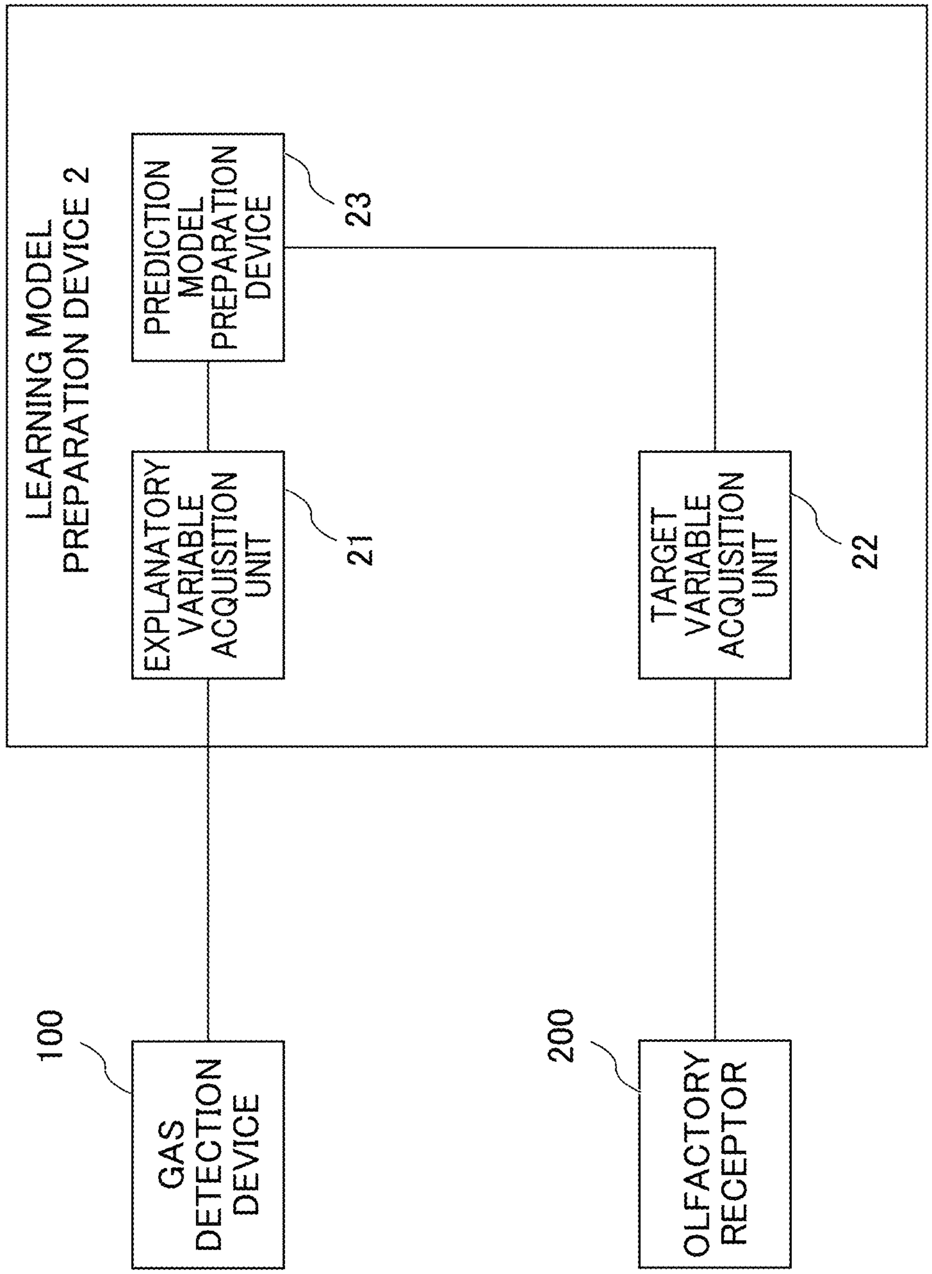
FIG. 7 is a block diagram illustrating a prediction model preparation device according to a second embodiment of the present invention.

The following describes a prediction model preparation device 2, a prediction model preparation method, and a program according to a second embodiment of the present invention with reference to FIG. 7. In the description of the second embodiment, the same elements of configuration as their corresponding elements in the foregoing embodiment are denoted by the same reference numerals, and description of such elements will be omitted or simplified. The prediction model preparation device 2, the prediction model preparation method, and the program according to the second embodiment are a device, a method, and a program for preparing the prediction model according to the first embodiment.

The prediction model preparation device 2 prepares a prediction model for converting output information outputted from a gas detection device 100 for a specific odor molecule into quantified data. As shown in FIG. 6, the prediction model preparation device 2 includes an explanatory variable acquisition unit 21, a target variable acquisition unit 22, and a prediction model preparation unit 23.

The explanatory variable acquisition unit 21 is, for example, implemented through operation of a CPU. The explanatory variable acquisition unit 21 acquires, as an explanatory variable, output information outputted from a plurality of gas detection devices 100 respectively corresponding to a plurality of odor molecules. For example, the explanatory variable acquisition unit 21 may acquire, as output information, the sum or average of outputs of the plurality of gas detection devices 100 (for example, 20 gas detection devices 100), the presence or absence of a response, various indicators, the product of features of outputs and the number of gas detection devices 100, or the product of time-series data and the number of feature patterns and the number of gas detection devices 100.

The target variable acquisition unit 22 is, for example, implemented through operation of the CPU. The target variable acquisition unit 22 acquires, as a target variable, response information indicating responses of a plurality of olfactory receptors 200 respectively corresponding to the plurality of odor molecules. For example, the target variable acquisition unit 22 may acquire, as output information, the sum or average of outputs from the olfactory receptors 200 (for example, 400 spots), the presence or absence of a response, various indicators, the product of features of outputs and the number of spots of the olfactory receptors 200, or the product of time-series data and the number of feature patterns and the number of spots of the olfactory receptors 200.

The prediction model preparation unit 23 is, for example, implemented through operation of the CPU. The prediction model preparation unit 23 prepares a prediction model by applying the acquired explanatory variable and the acquired target variable to machine learning. The prediction model preparation unit 23 prepares a prediction model using methods such as correlation coefficient, principal component analysis, and logistic regression.

The following describes operation of the prediction model preparation device 2 (prediction model preparation method). First, the explanatory variable acquisition unit 21 acquires output information as an explanatory variable. Next, the target variable acquisition unit 22 acquires response information as a target variable. Next, the prediction model preparation unit 23 prepares a prediction model using the explanatory variable and the target variable.

The following describes the program according to the present embodiment. Each of the components included in the prediction model preparation device 2 can be implemented by hardware, software, or a combination thereof. Being implemented by software herein means being implemented through a computer reading and executing a program.

The program can be supplied to the computer by being stored on any of various types of non-transitory computer readable media. The non-transitory computer readable media include various types of tangible storage media. Examples of non-transitory computer readable media include magnetic storage media (such as flexible disks, magnetic tape, and hard disk drives), magneto-optical storage media (such as magneto-optical disks), compact disc read only memory (CD-ROM), compact disc recordable (CD-R), compact disc rewritable (CD-R/W), and semiconductor memory (such as mask ROM, programmable ROM (PROM), erasable PROM (EPROM), flash ROM, and random access memory (RAM)). Alternatively, a display program may be supplied to the computer using any of various types of transitory computer readable media. Examples of transitory computer readable media include electrical signals, optical signals, and electromagnetic waves. Such transitory computer readable media are able to supply the program to the computer through a wireless communication channel or a wired communication channel such as electrical wires or optical fibers.

As described above, the prediction model preparation device 2, the prediction model preparation method, and the program according to the second embodiment produce the following effects.

(7) A prediction model preparation device 2 for preparing a prediction model for converting output information outputted from a gas detection device 100 for a specific odor molecule into quantified data, the prediction model preparation device including: an explanatory variable acquisition unit 21 configured to acquire, as an explanatory variable, output information outputted from a plurality of gas detection devices 100 respectively corresponding to a plurality of odor molecules; a target variable acquisition unit 22 configured to acquire, as a target variable, response information indicating responses of a plurality of olfactory receptors 200 respectively corresponding to the plurality of odor molecules; and a prediction model preparation unit 23 configured to prepare a prediction model by applying the acquired explanatory variable and the acquired target variable to machine learning. This configuration allows for preparation of a prediction model for converting output information obtained from various gas detection devices 100 into response information and outputting the thus obtained response information. The prediction model preparation device 2 allows for quantification of output information through the conversion into response information, making it possible to configure a conversion device 1 that can establish a correlation between the gas detection devices 100.

Third Embodiment

Figure 8:
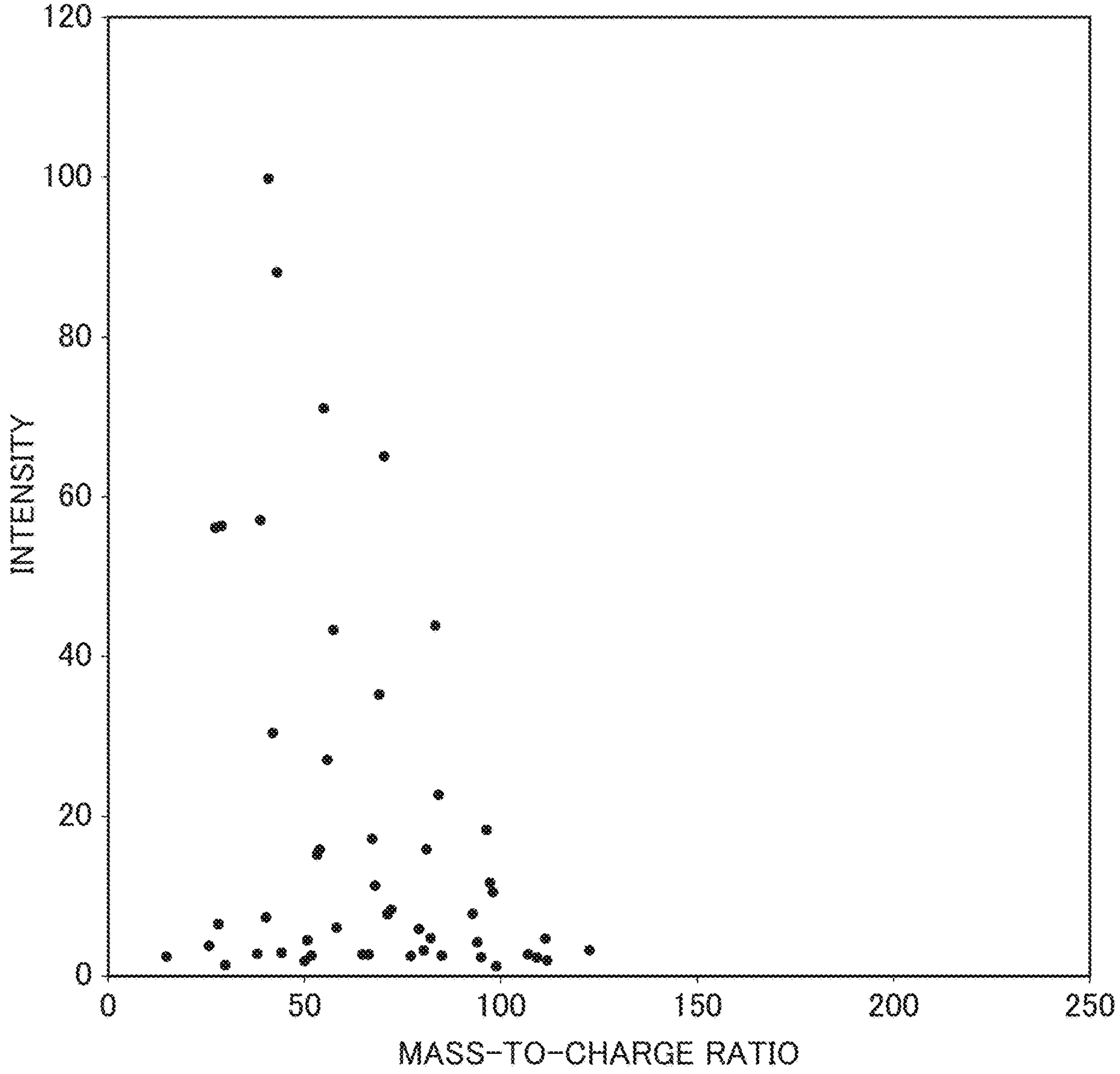
FIG. 8 is a graph showing an example of a plot used as an explanatory variable when conversion was performed using a conversion device according to a third embodiment of the present invention.
Figure 9:
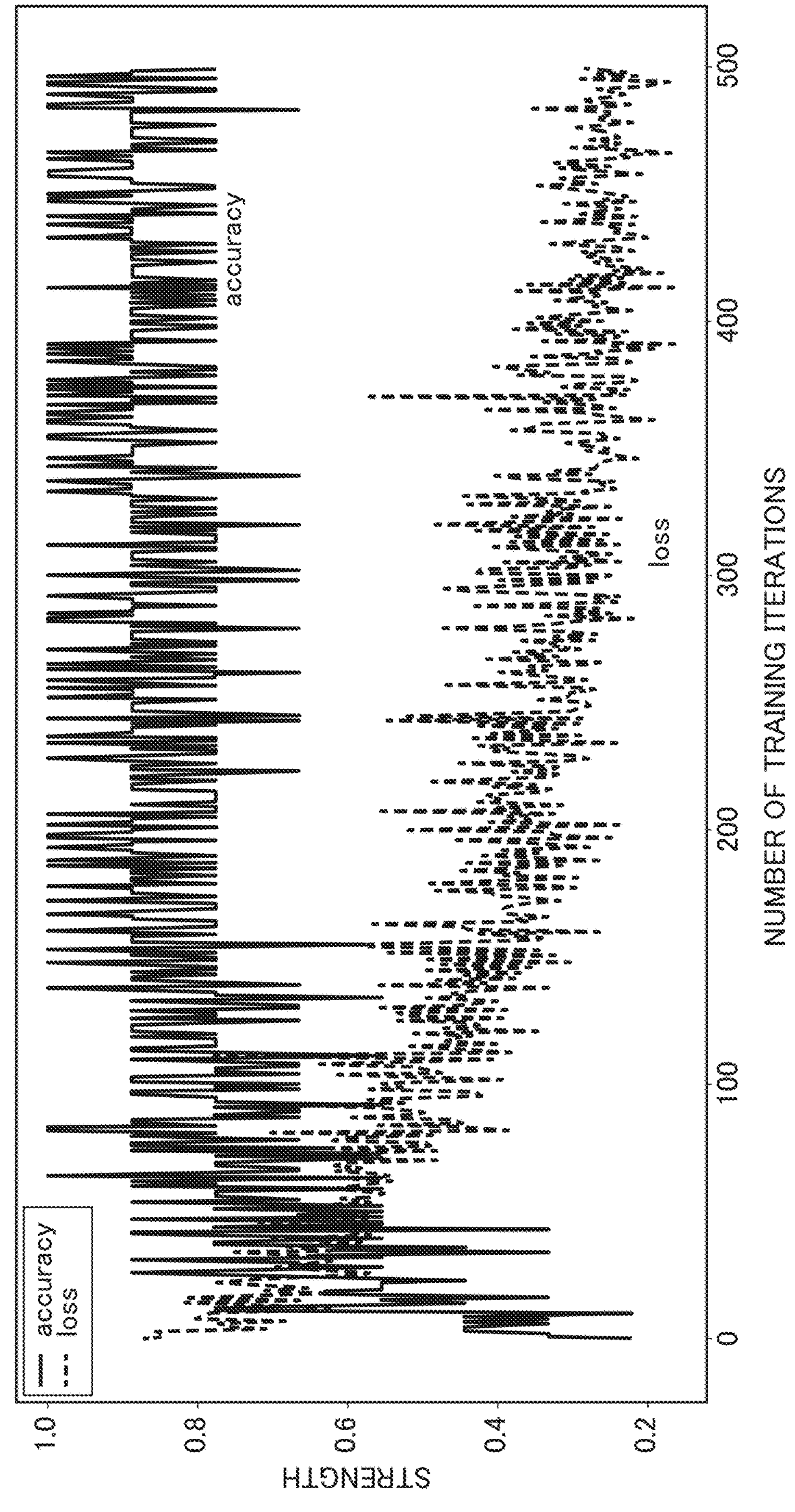
FIG. 9 is an example of a graph showing correlation between values of a target variable predicted through conversion performed using the conversion device according to the third embodiment and values obtained after conversion.

The following describes a conversion device 1, a conversion information preparation method, and a program according to a third embodiment of the present invention with reference to FIG. 8 and FIG. 9. In the description of the third embodiment, the same elements of configuration as their corresponding elements in the foregoing embodiments are denoted by the same reference numerals, and description of such elements will be omitted or simplified.

The conversion device 1 according to the third embodiment differs from those according to the first and second embodiments in that the former uses mass spectrometers (gas chromatograph-mass spectrometers) as gas detection devices 100. The conversion device 1 according to the third embodiment also differs from those according to the first and second embodiments in that the former uses outputs from the gas detection devices 100 (mass spectrometers) as output information. The conversion device 1 according to the third embodiment acquires, as output information, a collection of plots representing intensity plotted against mass-to-charge ratio outputted from each gas detection device 100. For example, the conversion device 1 acquires, as output information, a collection of plots representing intensity plotted against mass-to-charge ratio obtained as a result of the gas detection device 100 detecting a gaseous compound. That is, the conversion device 1 acquires, as output information, data of mass-to-charge ratio of fragment ions (including noise) generated when gas molecules are ionized, prior to a process of identifying the molecular structure of the gaseous compound by the gas detection device 100. The conversion device 1 also converts output information into response information indicating a response of an olfactory receptor 200 using a prediction model trained using the mass-to-charge ratio data (including noise) as an explanatory variable. Thus, the conversion device 1 converts output information into response information indicating a response of an olfactory receptor, regardless of differences in characteristics between the gas detection devices 100. It should be noted that the gas detection devices 100 are not limited to performing detection, and may perform collection, measurement, and analysis.

The following describes an Example of the third embodiment.

Example 3

With respect to each of the gas detection devices 100, data was acquired as described below. An odor molecule solution was diluted 10000-fold with a solvent, and then 1 μL of the diluted solution was collected using a syringe and put into the gas detection device 100. Mass-to-charge ratio data obtained for each molecular species during the detection was used for conversion. The same experimental conditions and procedures as in Example 1 were used for an array sensor including olfactory receptor-expressing cells.

As in Example 1, data processing was performed through regression analysis by a Random Forest method to prepare a model. Python was used as the language. A supervised learning method was employed. The model was evaluated using the coefficient of determination. Processing of the mass-to-charge ratio data obtained from the gas detection devices 100 involved representing the data in the form of a graph as shown in FIG. 8 and reading the intensity for each pixel of the resulting image. The thus read data was used as output information. The output information from the gas detection devices 100 (mass spectrometers) was used as an explanatory variable, and response information indicating responses of the olfactory receptors 200 was used as a target variable.

Analysis was performed on the resulting model, successfully obtaining an R-squared value of 0.828, as shown in FIG. 9 where the vertical axis represents predicted values (response information) outputted from the prediction model and the vertical axis represents actual values of the target variable (activation levels of olfactory receptor 200-expressing cells).

As described above, the prediction model preparation device 2, the prediction model preparation method, and the program according to the third embodiment produce the following effects.

(8) The conversion unit 12 uses, as output information, an output signal from a mass spectrometer adopted as a gas detection device 100. This configuration allows the conversion device 1 to establish a correlation between the gas detection devices 100 by converting output information into response information even in a case where mass spectrometers are adopted. In particular, the use of mass-to-charge ratio data (including noise) as output information allows for a reduction in time from the collection of the gaseous compound to the conversion by the conversion unit 12 into response information indicating a response of an olfactory receptor 200, compared to a configuration in which data obtained after molecular structure identification is used as output information. Furthermore, since data to be used in this configuration is closer to data obtained upon the detection (raw data) than in the configuration in which data obtained after molecular structure identification is used as output information, it is possible to provide a conversion device 1 that offers a higher coefficient of determination (a more accurate conversion device 1).

The conversion device, the prediction model preparation device, the conversion information preparation method, the prediction model preparation method, and the program according to preferred embodiments of the present invention have been described above. However, the present disclosure is not limited to the embodiments described above, and changes may be made thereto as appropriate.

For example, in any of the embodiments described above, responses of the olfactory receptors 200 may be used as an explanatory variable, and output from the gas detection devices 100 may be used as a target variable. That is, the conversion device 1 may convert response information indicating a response of an olfactory receptor 200 to a specific odor molecule into quantified data to be outputted from a gas detection device 100. Specifically, the conversion device 1 may include: a response information acquisition unit (not shown) configured to acquire response information indicating a response of an olfactory receptor 200 to a specific odor molecule; a conversion unit 12 configured to convert the acquired response information into output information to be outputted from a gas detection device 100 using a prediction model trained through machine learning using response information indicating responses of a plurality of olfactory receptors 200 respectively corresponding to a plurality of odor molecules as an explanatory variable and output information outputted from a plurality of gas detection devices 100 respectively corresponding to the plurality of odor molecules as a target variable; and an output unit 14 configured to output the output information obtained through the conversion. This configuration makes it possible to design the gas detection devices 100 using the response information of the olfactory receptors 200. For example, the response information can be used to design gas detection devices 100 that respond to a specific range of response information. That is, responses of the olfactory receptors 200 can be used as a measurement reference.

In any of the embodiments described above, the conversion device 1 may include a determination unit (not shown) configured to determine that a gas detection device 100 is experiencing a malfunction if response information obtained through the conversion of output information from the gas detection device 100 is out of a predetermined range. The output unit 14 may output the result of the determination by the determination unit. This configuration allows for an improvement in versatility of the conversion device 1.

In any of the embodiments described above, gas detection devices 100 to be subjected to odor exposure may be changed depending on the odor of gas. For example, outputs from gas detection devices 100 that respond to (are highly responsive to) the odor of gas may be used as output information. This configuration allows for an improvement in the learning efficiency. This configuration also allows for development of a flexible conversion device 1 that takes into account capabilities and limitations of each gas detection device 100.

In the third embodiment described above, gas chromatograph-mass spectrometers are used as the gas detection devices 100. However, the present invention is not limited as such. Devices that do not have gas chromatography functionality may be used as the gas detection devices 100. Furthermore, the gas detection devices 100 may be direct analysis in real time-mass spectrometry (DART-MS) devices. The gas detection devices 100 may be atmospheric pressure mass spectrometers for analysis at atmospheric pressure.

In the first embodiment described above, the estimation unit 13 is described as being configured to estimate a descriptor representing a characteristic (sensory characteristic) of the odor. However, the present invention is not limited as such. The estimation unit 13 may estimate various types of information as long as the information is associated with response information for conversion that indicates a response of an olfactory receptor 200. Specifically, the estimation unit 13 may estimate, for example, the intensity of the odor, a color recalled when the odor is perceived, the pleasantness or unpleasantness of the odor, or whether or not the odor is familiar to the sense of smell.

In the embodiments described above, the conversion unit 12 is described as being configured to perform the conversion using a prediction model trained through machine learning. However, the present invention is not limited as such. The conversion unit 12 may perform the conversion without using a prediction model trained through machine learning.

In any of the embodiments described above, the conversion device 1 may transfer predicted response information (response information obtained through the conversion) indicating a response of an olfactory receptor 200 to another device for secondary use.

The invention claimed is:

1. A conversion device for converting output information outputted from a gas detection-capable device for a specific odor molecule into response information indicating a response of an olfactory receptor, the conversion device comprising:

an output information acquisition unit configured to acquire output information outputted from a gas detection-capable device for a specific odor molecule;

a conversion unit configured to convert the acquired output information into response information based on output signals outputted from a plurality of gas detection-capable devices respectively corresponding to a plurality of odor molecules and response information indicating responses of a plurality of olfactory receptors respectively corresponding to the plurality of odor molecules; and an output unit configured to output the response information obtained through the conversion, wherein different types of nucleic acids are arranged on a substrate with space from each other and the plurality of olfactory receptors are transiently expressed by cells that are brought into contact with the nucleic acids on the substrate, and wherein the response information corresponds to the activation levels of the olfactory receptors that are quantitatively evaluated by measuring changes caused by the plurality of odor molecules.

2. The conversion device according to claim 1, wherein the conversion unit converts the acquired output information into response information indicating a response of an olfactory receptor using a prediction model trained through machine learning using output information outputted from the plurality of gas detection-capable devices respectively corresponding to the plurality of odor molecules as an explanatory variable and the response information indicating responses of the olfactory receptors respectively corresponding to the plurality of odor molecules as a target variable.

3. The conversion device according to claim 2, wherein the conversion unit uses a prediction model trained through machine learning using, as an explanatory variable, a numerical value, a function, or a spatial or temporal indicator that is calculated using a mathematical, statistical, or machine learning technique from the output information outputted from each of the gas detection-capable devices, or a variable newly created through feature engineering.

4. The conversion device according to claim 2, wherein the conversion unit uses a prediction model trained through machine learning using, as a target variable, a numerical value, a function, or a spatial or temporal indicator that is calculated using a mathematical, statistical, or machine learning technique from the response information of each of the olfactory receptors, or a variable newly created through feature engineering.

5. The conversion device according to claim 1, wherein the conversion unit converts the acquired output information into response information using a prediction model trained through machine learning using time-series data and the number of feature patterns from the output information outputted from each of the plurality of gas detection-capable devices as an explanatory variable, and time-series data and the number of feature patterns from the response information of the plurality of olfactory receptors as a target variable.

6. The conversion device according to claim 1, wherein the conversion unit uses a prediction model trained through machine learning using, as an explanatory variable, a presence or absence of output information from each of the plurality of gas detection-capable devices.

7. The conversion device according to claim 1, wherein the conversion unit uses a prediction model trained through machine learning using, as a target variable, a presence or absence of a response of each of a plurality of receptors included in the olfactory receptors.

8. The conversion device according to claim 2, wherein the conversion unit uses a prediction model trained through machine learning using, as an explanatory variable, mass-to-charge ratio and intensity based on the output information outputted from each of the gas detection-capable devices.

9. The conversion device according to claim 1, further comprising an estimation unit configured to estimate a descriptor representing a characteristic of the specific odor from the response information obtained through the conversion, wherein the output unit outputs the thus estimated descriptor.

* * * * *